US00PP26622P3

(12) United States Plant Patent
Korlipara

(10) Patent No.: US PP26,622 P3
(45) Date of Patent: Apr. 19, 2016

(54) ***GEUM* PLANT NAMED 'SUNKISSED LIME'**

(50) Latin Name: ***Geum* hybrid**
Varietal Denomination: Sunkissed Lime

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 98 days.

(21) Appl. No.: 14/120,894

(22) Filed: Jul. 8, 2014

(65) Prior Publication Data

US 2016/0014945 P1 Jan. 14, 2016

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — June Hwu
(74) *Attorney, Agent, or Firm* — Klarquist Sparkman, LLP

(57) ABSTRACT

A new and distinct *Geum* plant named 'Sunkissed Lime' characterized by orange single to semi-double flowers in cymes, lime green to yellow foliage, a dense, mounding habit, spring bloom with sporadic summer to fall bloom, and excellent vigor.

1 Drawing Sheet

Botanical designation: *Geum* hybrid.
Variety denomination: 'Sunkissed Lime'.

BACKGROUND OF THE INVENTION

The present invention relates to a new and distinct cultivar of *Geum* plant given the name 'Sunkissed Lime'. *Geum* is in the family Rosaceae. The new cultivar originated from a planned breeding program to produce a gold foliage *Geum* with good vigor and flowering. The parents were unnamed proprietary seedlings from interspecific crosses.

Compared to *Geum coccineum* 'Eos' (unpatented), the new cultivar has a larger habit, is more vigorous, with flowers orange rather than red orange, with flowers in cymes rather than solitary, and with a much longer bloom time.

Compared to the parents, the new cultivar has lime green foliage rather than green.

SUMMARY OF THE INVENTION

The following traits have been repeatedly observed and are determined to be the unique characteristics of 'Sunkissed Lime'. These characteristics in combination distinguish 'Sunkissed Lime' as a new and distinct cultivar:

1. orange single to semi-double flowers in cymes,
2. lime green to yellow foliage,
3. a dense, mounding habit,
4. spring bloom with sporadic summer to fall bloom, and
5. excellent vigor.

This new cultivar has been reproduced only by asexual propagation (stem tip cuttings and tissue culture from apical buds). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a one-year-old *Geum* 'Sunkissed Lime' growing in the trial bed in shade in October in Canby, Oreg.

FIG. 2 shows a one-year-old *Geum* 'Sunkissed Lime' growing in the trial bed in sun in April in Canby, Oreg.

DETAILED PLANT DESCRIPTION

The following is a detailed description of the new *Geum* cultivar based on observations of a one-year-old specimen grown in full sun in the trial bed in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart*, 5$^{th}$ edition.

Plant:

*Type*.—Herbaceous perennial.
*Hardiness*.—USDA Zone 5-9.
*Size*.—39 cm wide and 22 cm tall to top of the foliage.
*Form*.—Mound.
*Vigor*.—Excellent.
*Number of rosettes*.—About 50.

Stem: None.

Leaf:

*Type*.—Pinnately compound.
*Arrangement*.—Rosette.
*Blade*.—Grows to 13.5 cm long and 9 cm wide, shape spatulate overall, 7 to 11 leaflets; terminal leaflet the largest, reniform, grows to 6 cm long and 9 cm wide, shallowly cut 4 to 6 times, tip obtuse, bases cuneate, pubescent on both sides, veins pinnate and impressed, color topside Yellow Green 144A lightening in high light to Yellow 11A and darkening in low light to Green 137A, veins 144A; bottom side closest to 145A, lightening to Yellow 11A in high light and darkening to 147B in low light, veins 146D.

*Petiole*.—Sessile and clasping, rachis pubescent, Yellow Green 146D tinted Greyed Purple 187B.

*Color*.—Topside Green 137A including veins, bottom side Yellow Green 146B with veins 146C.

Inflorescence:

*Description*.—In cymes with 5 to 8 single to semi-double flowers.

*Size of inflorescence*.—Grows to 8 cm wide and 16.5 mm deep.

*Peduncle*.—Grows to 15 cm tall and 4 mm wide, pubescent, Yellow Green 146D tinted Greyed Purple 187B; 1 to 10 cauline leaves decreasing in size up the stem, sessile, grow to 10 cm long and 6 cm wide, ovate overall, margin deeply divided and lobed with 1 to 5 leaflets, tip acuminate, base usually cuneate, pubescent on both sides, color topside Yellow Green 144A lightening in high light to Yellow 11A and darkening in low light to Green 137A, veins 144A; bottom side closest to 145A, lightening to Yellow 11A in high light and darkening to 147B in low light, veins 146D.

*Pedicel*.—Variable 0.5 cm to 2.5 cm long and 1 mm wide, pubescent, closest to Yellow Green 145C.

Flower bud:

*Size*.—7 mm deep and 8 mm wide.

*Shape*.—Ovoid.

*Surface*.—Pubescent.

*Color*.—Yellow Green 145C.

Flower:

*Type*.—Actinomorphic.

*Size*.—30 mm wide and 10 mm deep.

*Corolla description*.—5 to 9 petals (usually terminal flower semi-double with 9 petals, lateral flowers single with 5 petals), each obcordate and notched to incised at tip, entire to sinuate margins, base cuneate, grows to 10 mm long and 14 mm wide, glabrous on both sides, top side Orange 28A lightening to 26A, bottom side Orange 26C.

*Calyx description*.—5 sepal lobes, alternating with epicalyx segments (each 5 mm long and less than 1 mm wide), stellate, 7 mm deep and 29 mm wide, tube bowl shaped 9 mm wide and 2 mm deep, lobes triangular 11 mm long and 4 mm wide at base, margins entire, tip acuminate, pubescent outside and glabrous inside, Green Yellow 1C on top and bottom sides.

*Pistil description*.—8 mm long and 6 mm wide, ovary 3 mm long and 5 mm wide, Yellow Green 144A, about 100 styles and stigmas, styles 4 mm long, Yellow Green 144A at base blending to Yellow Orange 16A at top; stigmas Yellow Orange 17A.

*Stamen description*.—About 200, 6.5 mm long, filaments 6 mm long, Yellow Orange 23A, anthers 0.5 mm long, Yellow Orange 23A, pollen none.

*Fragrance*.—None.

*Lastingness*.—Each flower last approximately one week in summer and up to two weeks in cool weather.

*Bloom time*.—April to June with sporadic rebloom through October in Canby, Oreg.

Fruit: None observed to date.

Seed: None, sterile.

Disease and pests: The new cultivar is typical to the genus. No known resistances to pests or diseases. No problems have been found in Canby, Oreg.

I claim:

1. A new and distinct *Geum* plant as herein illustrated and described.

* * * * *

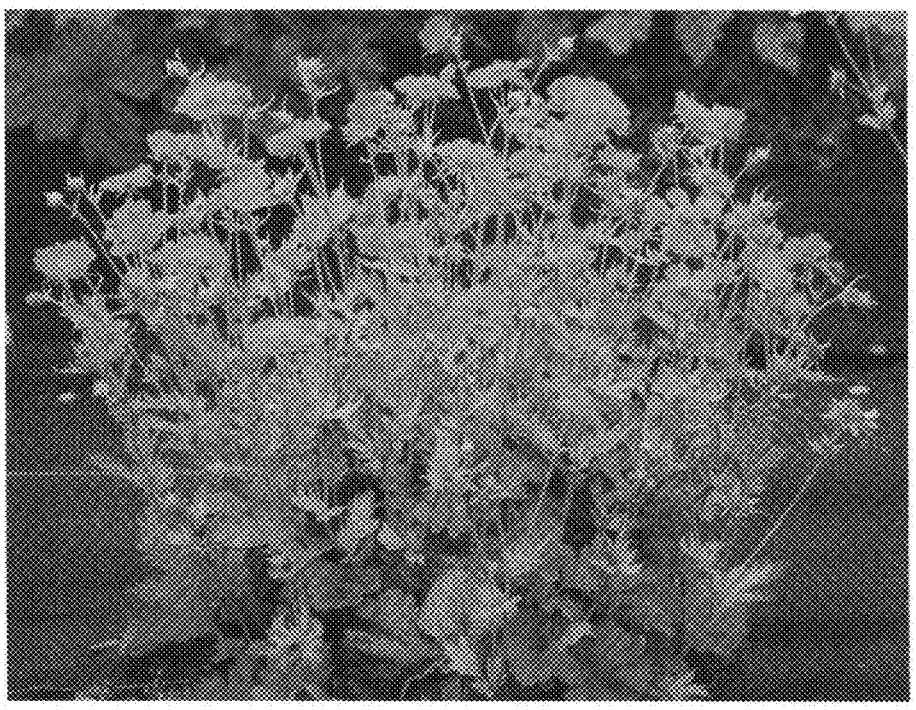

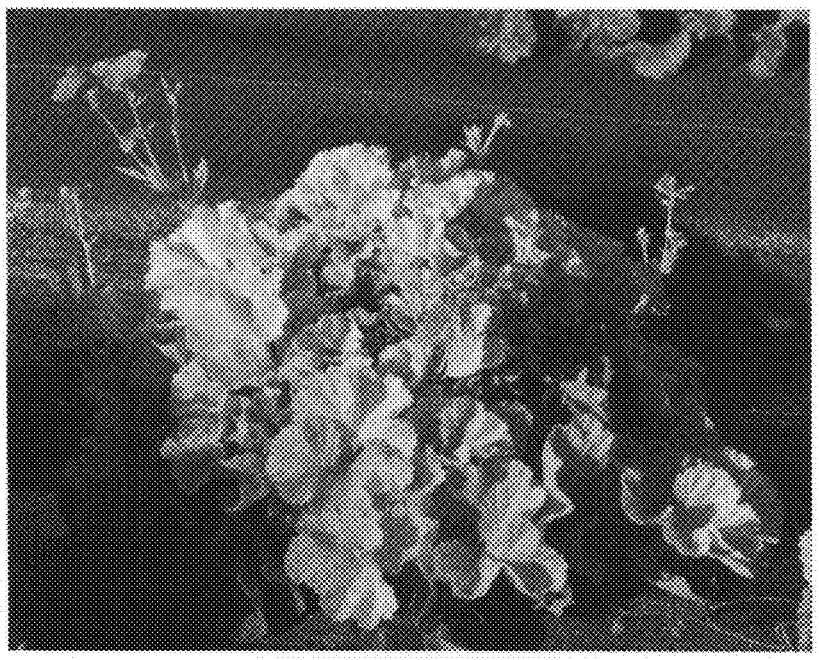
FIG. 1 above, FIG. 2 below